United States Patent [19]

Jackson et al.

[11] Patent Number: 5,516,946
[45] Date of Patent: May 14, 1996

[54] PRODUCING $CF_3CH_2CF_3$ AND/OR $CF_3CH=CF_2$ BY THE CONVERSION OF FLUORINATED ETHERS

[75] Inventors: Scott C. Jackson, Kennett Square, Pa.; Paul R. Resnick; Steven H. Swearingen, both of Wilmington, Del.

[73] Assignee: E. I. Du Pont de Nemours and Company, Wilmington, Del.

[21] Appl. No.: 392,426

[22] Filed: Feb. 22, 1995

Related U.S. Application Data

[62] Division of Ser. No. 267,988, Jun. 29, 1994, Pat. No. 5,420,368.

[51] Int. Cl.⁶ .................................................. C07C 17/02
[52] U.S. Cl. ........................................ 570/153; 570/177
[58] Field of Search ................................ 570/153, 177

[56] References Cited

FOREIGN PATENT DOCUMENTS 0002098  5/1979  European Pat. Off. .

OTHER PUBLICATIONS

Hall, C. R. et al, *Chem. Ind.* (London), 5, 145–146 (1989).
Koshar, R. J. et al, *Addition of Alcohols to Octafluoroisobutene*, 79, 1741–1744 (Apr. 1957).

Kocharyan, S. T. et al, "Alkylating Properties of Alkyl Perfluoroisobutenyl Ethers. Communication 1. Complexes of Alkyl Perfluoroisobutenyl Ethers with Trialkylamines", translated from *Izvestiya Akademii Nauk SSSR, Seriya Khimicheskaya*, 5, 846–854, Apr. 1968 (Institute of Heteroorganic Compounds, Academy of Sciences of the USSR).

*Primary Examiner*—Alan Siegel

[57] ABSTRACT

A process is disclosed for producing $CF_3CH_2CF_3$ and/or $CF_3CH=CF_2$ from at least one ether compound selected from the group consisting of compounds having the formula $(CF_3)_2CHCF_2OR$ and compounds having the formula $(CF_3)_2C=CFOR$ (wherein R is an alkyl group of the formula $C_nH_{2n+1}$ and n is an integer from 1 to 6) by contacting the ether compound(s) with water at an elevated temperature of at least about 75° C. The reaction of ether compound(s) with water may be employed in connection with a process for producing tetrafluoroethylene and/or hexafluoropropylene by pyrolysis, where by-product perfluoroisobutylene is reacted with an alkanol to produce the ether compound(s).

7 Claims, No Drawings

PRODUCING $CF_3CH_2CF_3$ AND/OR $CF_3CH=CF_2$ BY THE CONVERSION OF FLUORINATED ETHERS

This is a division of application Ser. No. 08/267,988, filed Jun. 29, 1994 now U.S. Pat. No. 5,420,368.

FIELD OF THE INVENTION

This invention relates to processes for the manufacture of hydrofluorocarbons (i.e., HFCs) and more particularly to processes for the production of 1,1,1,3,3,3-hexafluoropropane and/or 1,1,1,3,3-pentafluoropropene.

BACKGROUND

Tetrafluoroethylene and hexafluoropropylene are commonly manufactured by high temperature pyrolysis. In these manufacturing processes, minor amounts of highly toxic perfluoroisobutylene are typically produced. This material can be reacted with alkanols to form ethers. Typically, perfluoroisobutylene is reacted with methanol to convert it to two less toxic ether compounds, $(CF_3)_2CHCF_2OCH_3$ (herein designated "ether A" and $(CF_3)_2C=CFOCH_3$ (herein designated "ether B") (see, e.g., European Patent Publication No. 0 002 098). While ether A and ether B are much less hazardous than the perfluoro compound from which they are prepared, they still are generally disposed of as waste product. There is interest in developing means for productive use of ether materials such as ether A and ether B.

SUMMARY OF THE INVENTION

A process is provided in accordance with this invention for producing 1,1,1,3,3,3-hexafluoropropane and/or 1,1,1,3,3-pentafluoropropene from ether A, ether B, and/or said certain of their alkyl analogs. The process comprises the step of contacting at least one ether compound selected from the group consisting of compounds having the formula $(CF_3)_2CHCF_2OR$ and compounds having the formula $(CF_3)_2C=CFOR$, wherein R is an alkyl group of the formula $C_nH_{2n+1}$ and n is an integer from 1 to 6 (e.g., $CH_3$), with water at an elevated temperature of at least about 75° C. (optionally in the presence of an acid or base). The reaction of said ether compound(s) with water may be employed in connection with a process for producing tetrafluoroethylene and/or hexafluoropropylene by pyrolysis, where by-product perfluoroisobutylene is reacted with an alkanol to produce the ether compound(s).

DETAILED DESCRIPTION OF THE INVENTION

The present invention involves the discovery that ether compounds of the formula $(CF_3)_2CHCF_2OR$ and of the formula $(CF_3)_2C=CFOR$, when reacted with $H_2O$, are converted to 1,1,1,3,3,3-hexafluoropropane (i.e., $CF_3CH_2CF_3$ or HFC-236fa) and/or 1,1,1,3,3-pentafluoropropene (i.e., $CF_3CH=CF_2$ or HFC-1225zc). Accordingly, HFC-236fa and/or HFC-1225zc are produced in accordance with this invention by the reaction of water and $(CF_3)_2CHCF_2OR$ (i.e., the alkylfluorobutyl ether reactants of this invention), by the reaction of water and $(CF_3)_2C=CFOR$ (i.e., the alkylfluorobutenyl ether reactants of this invention), wherein R is a $C_1$ to $C_6$ alkyl group as defined above, or by the reaction of water with a mixture of such ether reactants (e.g., a mixture of the alkylfluorobutyl ether reactants and the alkylfluorobutenyl ether reactants of this invention).

$(CF_3)_2CHCF_2OR$ and $(CF_3)_2C=CFOR$ can be produced by reacting perfluoroisobutylene with alkanols. A typical procedure for the production of alkylfluorobutyl ethers and alkylfluorobutenyl ethers is disclosed by R. J. Koshar et al., J. Am. Chem. Soc., 79, 1741–44 (1957). The methyl ethers, $(CF_3)_2CHCF_2OCH_3$ (i.e., ether A) and $(CF_3)_2C=CFOCH_3$ (i.e., ether B), are preferred for use in this invention. These may be prepared by using methanol as the alkanol.

Inasmuch as perfluoroisobutylene is produced as a by-product (typically in small amounts) during the production of at least one of tetrafluoroethylene and hexafluoropropylene by pyrolysis (e.g., pyrolysis of chlorodifluoromethane) the present invention provides a convenient method of utilizing the by-product perfluoroisobutylene produced in a process for producing tetrafluoroethylene, hexafluoropropylene, or both tetrafluoroethylene and hexafluoropropylene by that pyrolysis, by reacting the perfluoroisobutylene with an alkanol of the formula ROH (where R is a $C_1$ to $C_6$ alkyl group as defined above) to produce $(CF_3)_2CHCF_2OR$ and/or $(CF_3)_2C=CFOR$, and then reacting these ether compounds with water as provided herein to produce HFC-236fa and/or HFC-1225zc.

$(CF_3)_2CHCF_2OR$ and $(CF_3)_2C=CFOR$, and particularly, ethers A and B may be reacted with water itself. Optionally acids (e.g., sulfuric acid, hydrochloric acid, acetic acid) or bases (e.g., sodium hydroxide, sodium bicarbonate, dimethylamine) may be present. The reaction may also be done in the presence of inert organic materials such as toluene.

The molar ratio of water to the ether reactant is normally about 1:1 or more, typically ranges from about 1:1 to about 100:1, and is preferably within the range of about 5:1 to about 75:1. The process of the present invention is suitably conducted at a temperature in the range of from about 75° C. to 500° C., and is preferably from about 150° C. to about 250° C. for liquid phase reactions, and from about 150° C. to 400° C. for vapor phase reactions. The reaction time is normally about 0.1 minute, or more, and typically ranges from about 0.1 minutes to about 24 hours.

The reaction of the alkylfluorobutyl ether reactants and/or the alkylfluorobutenyl ether reactants of this invention with water may be conducted in either the liquid or vapor phase. The reactions are normally conducted at pressures of 101 kPa to 7000 kPa, and for vapor phase reaction are preferably at elevated pressures (e.g., between about 1460 kPa and 2190 kPa). The reaction is preferably conducted in the presence of activated carbon. Activated carbon is particularly advantageous for embodiments where the ether compound is reacted in the vapor phase.

By "activated carbon" is meant an amorphous carbon having high adsorptivity for gases, vapors and colloidal solids. Such activated carbons are typically formed from the carbon source by heating to about 800° C. to 900° C. with steam or carbon dioxide to confer upon the carbon a porous internal structure. Any of the well known activated carbons can be used in the practice of this invention as well as any carbons prepared by techniques known in the art to improve carbon adsorptivity. Commercially available activated carbons useful in the process of this invention include those sold under the following trademarks: Darco™, Nuchar™, Columbia SBV™, Columbia MBV™, Columbia MBQ™, Columbia JXC™, Columbia CXC™, Calgon PCB™, and Barnaby Cheny NB™. The carbon can be in the form of powder, granules, or pellets, etc. However, it is preferred to use granules to facilitate use in tubular reactors. The size of the granules is not critical but it is preferred to employ granules having an average mesh size of about ¹⁄₂₅ to about ⅙ of the reactor diameter.

The process of this invention can be carried out readily using well known chemical engineering practice, which includes continuous, semi-continuous or batch operations. Lower temperatures, pressures and molar ratios of water to ethers, favor the formation of $CF_3CH=CF_2$ over $CF_3CH_2CF_3$. 1,1,1,3,3,3-Hexafluoropropane and 1,1,3,3,3-pentafluoropropene may be recovered from the reaction products by using conventional techniques such as decantation and/or distillation.

The reaction zone and its associated feed lines, effluent lines and associated units should be constructed of materials resistant to hydrogen fluoride. Typical materials of construction, well-known to the fluorination art, include stainless steels, in particular of the austenic type, the well-known high nickel alloys, such as Monel® nickel-copper alloys, Hastelloy® nickel-based alloys and, Inconel® nickel-chromium alloys, and copper-clad steel. Also suitable for reactor fabrication are such polymeric plastics as polytrifluorochloroethylene and polytetrafluoroethylene, generally used as linings.

HFC-236fa is useful as a refrigerant, fire extinguishant, heat transfer medium, gaseous dielectric, sterilant carrier, polymerization medium, particulate removal fluid, carrier fluid, buffing and abrasive agent, displacement drying agent and power cycle working fluid. In particular, HFC-236fa is highly effective and as a refrigerant for use in refrigeration equipment.

HFC-1225zc is useful as a monomer for the preparation of fluoropolymers.

Practice of the invention will become further apparent from the following non-limiting examples.

EXAMPLE 1

$(CF_3)_2C=CFOCH_3 + H_2O \rightarrow CF_3CH_2CF_3$

A mixture of 50 mL water, 25 mL concentrated sulfuric acid and 21.2 g $(CF_3)_2C=CFOCH_3$ (ether B) was heated in a Hastelloy™ nickel alloy tube for 6 hours at 200° C. The volatile gases were sampled and the infrared spectrum indicated that they were a mixture of carbon dioxide and $CF_3CH_2CF_3$ (HFC-236fa). An attempt to condense the volatiles by bleeding them into a dry ice cooled trap afforded 3 g of product which was a mixture of HFC-236fa with a small amount of carbon dioxide.

EXAMPLE 2

$(CF_3)_2C=CFOCH_3 + H_2O \rightarrow CF_3CH_2CF_3$

A mixture of 150 mL water and 31.8 g $(CF_3)_2C=CFOCH_3$ (ether B) was heated in a Hastelloy™ nickel alloy tube for 6 hours at 200° C. The gases were bubbled through a solution of aqueous NaOH and a $CaSO_4$ drying column, and condensed in a dry ice cooled trap to give 11.0 g of product. The IR, $^1H$ and $^{19}F$ NMR spectra showed it to be all $CF_3CH_2CF_3$. The yield was 48.2%.

EXAMPLE 3

$(CF_3)_2C=CFOCH_3 + H_2O \rightarrow CF_3CH_2CF_3$

A mixture of 50 mL water, 1 mL concentrated sulfuric acid and 10.0 g $(CF_3)_2C=CFOCH_3$ (ether B) was refluxed for 25 hr at 88°–90° C. The reaction mixture contained two layers. The 7.1 g lower organic layer was >80% starting material. The $^{19}F$ NMR spectrum of the upper aqueous layer showed it to contain HF and bifluoride. A small amount of trap material was obtained. The infrared spectrum showed it to be a mixture of carbon dioxide, HFC-236fa, and starting ether B.

EXAMPLE 4

$(CF_3)_2C=CFOCH_3 + H_2O \rightarrow CF_3CH_2CF_3$

A mixture of 50 g water and 15 g $(CF_3)_2C=CFOCH_3$ (ether B) was heated in a Hastelloy™ nickel alloy tube for 8 hours at 200° C. An infrared spectrum of the volatile product showed it to contain only carbon dioxide and $CF_3CH_2CF_3$ (HFC-236fa). The aqueous layer was acidic and the $^{19}F$ NMR spectrum showed the presence of HF and $HF_2^-$. No starting ether remained.

EXAMPLE 5

$(CF_3)_2CHCF_2OCH_3 + H_2O \rightarrow CF_3CH_2CF_3$

A 30 g mixture containing 92.7% $(CF_3)_2CHCF_2OCH_3$ (ether A) along with some ether B and toluene was heated in a Hastelloy™ nickel alloy tube with 150 mL water for 6 hours at 200° C. An infrared spectrum of the volatiles showed the presence of carbon dioxide and $CF_3CH_2CF_3$ (HFC-236fa). The gases were bubbled through a solution of aqueous NaOH and a $CaSO_4$ drying column, and condensed in a dry ice cooled trap to give 11.8 g (64.7%) HFC-236fa identified by its $^1H$ and $^{19}F$ NMR spectra. The aqueous residue contained HF and $HF_2^-$.

EXAMPLE 6

$(CF_3)_2C=CFOCH_3 + H_2O \rightarrow CF_3CH_2CF_3$

A mixture of 31.8 g $(CF_3)_2C=CFOCH_3$ (ether B) and 12.0 g sodium hydroxide was heated in a Hastelloy™ nickel alloy tube with 150 mL water for 3 hours at 200° C. An infrared spectrum of the volatiles showed the presence of carbon dioxide and $CF_3CH_2CF_3$ (HFC-236fa). The gases were bubbled through a solution of aqueous NaOH and a $CaSO_4$ drying column, and condensed in a dry ice cooled trap to give 3.0 g HFC-236fa. The aqueous residue was acidic and contained HF and $HF_2^-$.

EXAMPLE 7

$(CF_3)_2CHCF_2OCH_3 + (CF_3)_2C=CFOCH_3 + H_2O \rightarrow CF_3CH_2CF_3$

A 100 g mixture containing 59.0% $(CF_3)_2CHCF_2OCH_3$ (ether A), 20% $(CF_3)_2C=CFOCH_3$ (ether B), 15.9% toluene and 150 mL water was heated in a Hastelloy™ nickel alloy tube for 3 hours at 135° C. and 6 hours at 200° C. The volatiles were bubbled through a solution of aqueous NaOH and a $CaSO_4$ drying column, and condensed in a dry ice cooled trap to give 12.9 g HFC-236fa identified by its infrared spectrum. The liquid contents of the tube contained two layers. The upper layer, 14.9 g, was shown by $^1H$ and $^{19}F$ NMR spectroscopy to contain 16.5 wt. percent HFC-236fa and toluene. The combined HFC-236fa from the volatiles and the toluene corresponded to a yield of 15.4 g, 29.0% based on the starting ethers.

EXAMPLE 8

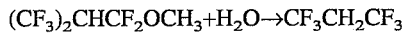

Activated carbon (25 g, ⅛" (0.32 mm) diameter pellets) and deionized water (5 g) were loaded into a 1" (2.54 cm) OD×12" (30.5 cm) length Inconel™ 600 nickel alloy tube. The reactor temperature was raised to 320° C. and the reactor pressure adjusted to 230 psig (1690 kPa). $(CF_3)_2CHCF_2OCH_3$ (ether A, 9.2 g) and deionized water (4.8 g) were independently and continuously fed to the reactor over 149 min. After the feed flow was stopped, the reactor was flushed with deionized water (10 g). After scrubbing the reactor effluent to remove HF, 6.9 g of fluorocarbon was isolated. GC analysis (area %) showed an 88% conversion of ether A to HFC-236fa with a selectivity of 93% and $CF_3CH=CF_2$ (HFC-1225zc) with a selectivity of 7%.

EXAMPLE 9

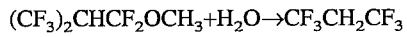

Activated carbon (25 g, ⅛" (0.32 mm) diameter pellets) and deionized water (5.8 g) were loaded into a 1" (2.54 cm) OD×12" (30.5 cm) length Inconel™ 600 nickel alloy tube. The reactor temperature was raised to 280° C. and the reactor pressure adjusted to 230 psig (1690 kPa). $(CF_3)_2CHCF_2OCH_3$ (ether A, 6.8 g) and deionized water (6.7 g) were independently and continuously fed to the reactor over 116 minutes. After the feed flow was stopped, the reactor was flushed with deionized water (11.2 g). After scrubbing the reactor effluent to remove HF, 3.3 g of fluorocarbon was isolated. GC analysis (area %) showed a 57% conversion of ether A to HFC-236fa with a selectivity of 85% and $CF_3CH=CF_2$ (HFC-1225zc) with a selectivity of 15%.

EXAMPLE 10

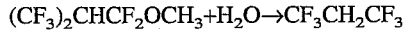

Activated carbon (25 g, ⅛" (0.32 mm) diameter pellets) and deionized water (10 g) were loaded into a 1" (2.54 cm) OD×12" (30.5 cm) length Inconel™ 600 nickel alloy tube. The reactor temperature was raised to 350° C. and the reactor pressure adjusted to 0 psig (101 kPa). $(CF_3)_2CHCF_2OCH_3$ (ether A, 53.4 g) and deionized water (21 g) were independently and continuously fed to the reactor over 185 minutes. After the feed flow was stopped, the reactor was flushed with deionized water (10 g). After scrubbing the reactor effluent to remove HF, 30.8 g of fluorocarbon was isolated. GC analysis (area %) showed an 87% conversion of ether A to HFC-236fa with a selectivity of 19% and $CF_3CH=CF_2$ (HFC-1225zc) with a selectivity of 66%. Other fluorocarbons produced included $(CF_3)_2CHCH_3$ and $CF_3(CH_3)C=CF_2$.

EXAMPLE 11

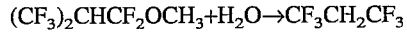

Activated carbon (25 g, ⅛" (0.32 mm) diameter pellets) and deionized water (5.3 g) were loaded into a 1" (2.54 cm) OD×12" (30.5 cm) length Inconel™ 600 nickel alloy tube. The reactor temperature was raised to 250° C. and the reactor pressure adjusted to 150 psig (1140 kPa). $(CF_3)_2CHCF_2OCH_3$ (ether A, 21.1 g) and deionized water (26.5 g) were independently and continuously fed to the reactor over 185 minutes. After the feed flow was stopped, the reactor was flushed with deionized water (10 g). After scrubbing the reactor effluent to remove HF, 6 g of fluorocarbon was isolated. GC analysis (area %) showed a 35% conversion of ether A to HFC-236fa with a selectivity of 56% and $CF_3CH=CF_2$ (HFC-1225zc) with a selectivity of 44%.

EXAMPLE 12

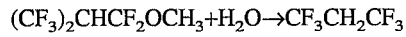

Activated carbon (25 g, ⅛" (0.32 mm) diameter pellets) and deionized water (20 g) were loaded into a 1" (2.54 cm) OD×12" (30.5 cm) length Inconel™ 600 nickel alloy tube. The reactor temperature was raised to 250° C. and the reactor pressure adjusted to 0 psig (101 kPa). $(CF_3)_2CHCF_2OCH_3$ (ether A, 21.5 g) and deionized water (40.6 g) were independently and continuously fed to the reactor over 185 minutes. After the feed flow was stopped, the reactor was flushed with deionized water (11.4 g). After scrubbing-the reactor effluent to remove HF, 9.9 g of fluorocarbon was isolated. GC analysis (area %) showed a 60% conversion of ether A to HFC-236fa with a selectivity of 22% and $CF_3CH=CF_2$ (HFC-1225zc) with a selectivity of 76%. Other fluorocarbons produced included $(CF_3)_2CHCH_3$ and $CF_3(CH_3)C=CF_2$.

EXAMPLE 13

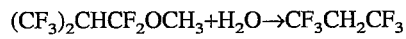

Activated carbon (25 g, ⅛41 (0.32 mm) diameter pellets) and deionized water (24.4 g) were loaded into a 1" (2.54 cm) OD×12" (30.5 cm) length Inconel™ 600 nickel alloy tube. The reactor temperature was raised to 175° C. and the reactor pressure adjusted to 30 psig (310 kPa). $(CF_3)_2CHCF_2OCH_3$ (ether A, 21 g) and deionized water (52.23 g) were independently and continuously fed to the reactor over 205 minutes. After the feed flow was stopped, the reactor was flushed with deionized water (10.0 g). After scrubbing the reactor effluent to remove HF, 3.5 g of fluorocarbon was isolated. GC analysis (area %) showed a 69% conversion of ether A to HFC-236fa with a selectivity of 33% and $CF_3CH=CF_2$ (HFC-1225zc) with a selectivity of 65%. Other fluorocarbons produced included $(CF_3)_2CHCH_3$ and $CF_3(CH_3)C=CF_2$.

EXAMPLE 14

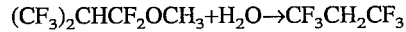

$(CF_3)_2CHCF_2OCH_3$ (ether A, 7.1 g) and deionized water (7.4 g) were independently and continuously fed to a 1" (2.54 cm) OD×12" (30.5 cm) length Inconel™ 600 nickel alloy tube over 60 minutes. The reactor was preheated to 450° C. and maintained at this temperature throughout the run. The reactor pressure was maintained at about atmospheric pressure. After scrubbing the reactor effluent to remove HF, 0.7 g of fluorocarbons were isolated. GC analysis (area %) showed an 11.% conversion of ether A to HFC-236fa with a selectivity of 11% and $CF_3CH=CF_2$ (HFC-1225zc) with a selectivity of 89%.

What is claimed is:

1. A process for producing at least one of tetrafluoroethylene and hexafluoropropylene by pyrolysis wherein perfluoroisobutylene is produced as a by-product and is reacted with an alkanol of the formula ROH, wherein R is an alkyl group of the formula $C_nH_{2n+1}$ and n is an integer from 1 to 6, to produce at least one ether compound selected from the group consisting of compounds of the formula $(CF_3)_2CHCF_2OR$ and compounds having the formula $(CF_3)_2C=CFOR$, characterized by:

reacting said at least one ether compound with water at an elevated temperature of at least about 75° C. to produce at least one compound selected from the group consisting of 1,1,1,3,3-hexafluoropropane and 1,1,1,3,3-pentafluoropropene.

2. The process of claim 1 wherein the ether compound is contacted with water at an elevated temperature in the presence of an acid or base.

3. The process of claim 1 wherein the ether compound is contacted with water in the presence of activated carbon.

4. The process of claim 3 wherein the ether compound is contacted with water in the vapor phase.

5. The process of claim 1 wherein $CF_3CH_2CF_3$ is produced.

6. The process of claim 1 wherein $CF_3CH=CF_2$ is produced.

7. The process of claim 1 wherein R is $CH_3$.

* * * * *